US00PP37136P2

(12) United States Plant Patent
van Langen

(10) Patent No.: US PP37,136 P2
(45) Date of Patent: Dec. 9, 2025

(54) ***ALOE* PLANT NAMED 'AMIAL2139'**

(50) Latin Name: *Aloe hybrida*
Varietal Denomination: AMIAL2139

(71) Applicant: NovoAmi B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 18 days.

(21) Appl. No.: 18/831,327

(22) Filed: Nov. 18, 2024

(51) Int. Cl.
*A01H 5/12* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 5/12; A01H 5/00
See application file for complete search history.

(56) References Cited

PUBLICATIONS https://www.floraldaily.com/article/9569321/amigo-plant-introduces-aloe-medivera/; Oct. 19, 2023; 4 pages.*
https://www.rhs.org.uk/plants/527189/aloe-tropical-(-amial2139-)/details; Mar. 5, 2025; 1 page.*

* cited by examiner

*Primary Examiner* — Kent L Bell
(74) *Attorney, Agent, or Firm* — Samuel R McCoy, Jr.

(57) ABSTRACT

A new and distinct *Aloe* plant named 'AMIAL2139' which is characterized by a rosette of succulent foliage that gives rise to an abundance of small, secondary rosettes which will eventually ring the entire primary rosette, foliage with an upright attitude, dark green foliage with a moderate abundance of light yellow-green, nearly white, oblong protuberances loosely arranged in highly irregular transverse rows on both the upper and lower leaf surfaces, dentate leaf margins with an abundance of spine-like teeth, and the stability of these characteristics from generation to generation.

3 Drawing Sheets

Latin name of the genus and species: The Latin name of the genus and species of the novel variety disclosed herein is *Aloe hybrida*.

Variety denomination: The inventive variety of *Aloe* disclosed herein has been given the variety denomination 'AMIAL2139'.

BACKGROUND OF THE INVENTION

Parentage: 'AMIAL2139' is a seedling selection resulting from the selected cross pollination of an unnamed interspecific *Aloe rouhii* x *Aloe descoingsii* hybrid plant (not patented), the seed parent, and an unnamed *Aloe vera* plant that typifies the species (not patented), the pollen parent. The crossing was made by the inventor in the spring of 2019 at a commercial greenhouse in Heerhugowaard, the Netherlands. In the spring of 2020, one seedling was observed which exhibited erect dark green foliage with an abundance of oblong foliar protuberances, unlike the parent plants and all other progeny in the trials. Upon confirmation of distinctness and stability, 'AMIAL2139' was selected for commercialization.

Asexual Reproduction: Asexual reproduction of the new cultivar 'AMIAL2139', by way of rooting leaf cuttings, was first initiated in the summer of 2020 at the inventor's commercial greenhouse in Heerhugowaard, the Netherlands. Through four subsequent generations, the unique features of this cultivar have proven to be stable and true to type.

SUMMARY OF THE INVENTION

The cultivar 'AMIAL2139' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIAL2139'. These characteristics in combination distinguish 'AMIAL2139' as a new and distinct *Aloe vera* plant:

1. 'AMIAL2139' exhibits a primary rosette of succulent foliage which gives rise to an abundance of small, secondary rosettes which will eventually ring the entire primary rosette with age; and
2. 'AMIAL2139' exhibits dark green succulent foliage which is held upright and slightly outward; and
3. 'AMIAL2139' exhibits dentate leaf margins with an abundance of spine-like teeth that are colored light greyed-green and lightly suffused with greyed-orange at their tips; and
4. 'AMIAL2139' exhibits a moderate abundance of light yellow-green, nearly white, oblong protuberances loosely arranged in highly irregular transverse rows on both the upper and lower leaf surfaces.

BOTANICAL DESCRIPTION OF THE PLANT

Figure 1:
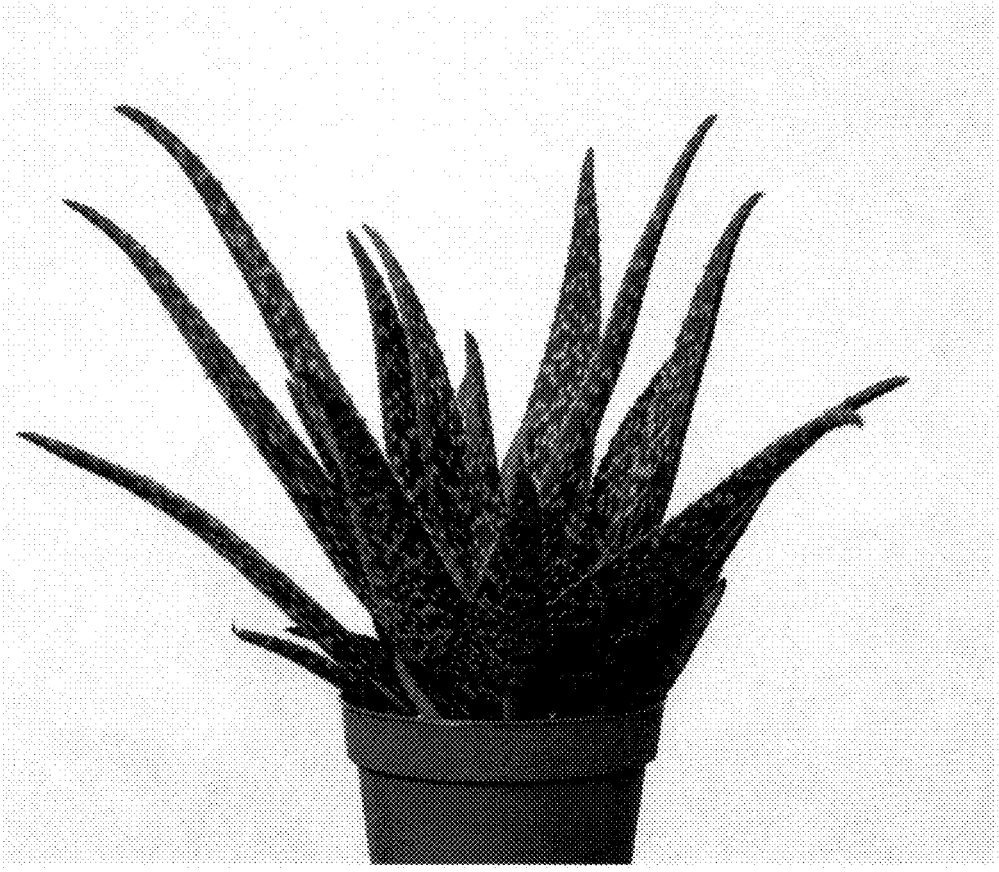
FIG. 1 illustrates, as nearly true as it is reasonably possible to make the same in color photographs of this type, an exemplary plant of 'AMIAL2139' grown in a commercial greenhouse in Honselersdijk, the Netherlands. This plant is approximately 40 weeks old, shown planted in a 14 cm container.
Figure 2:
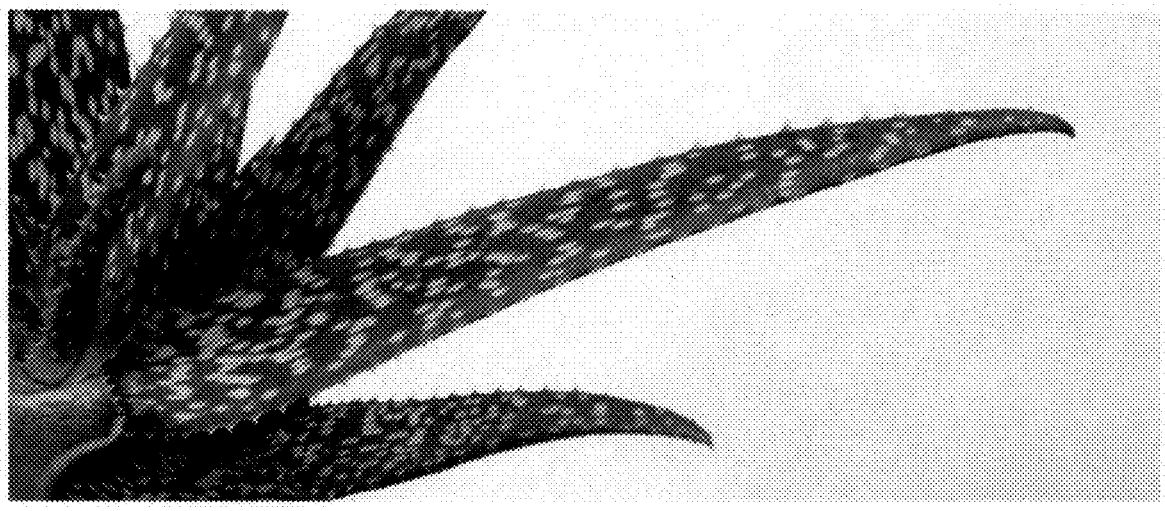
FIG. 2 illustrates, as nearly true as it is reasonably possible to make the same in color photographs of this type, adaxial surface of the mature foliage 'AMIAL2139'.
Figure 3:
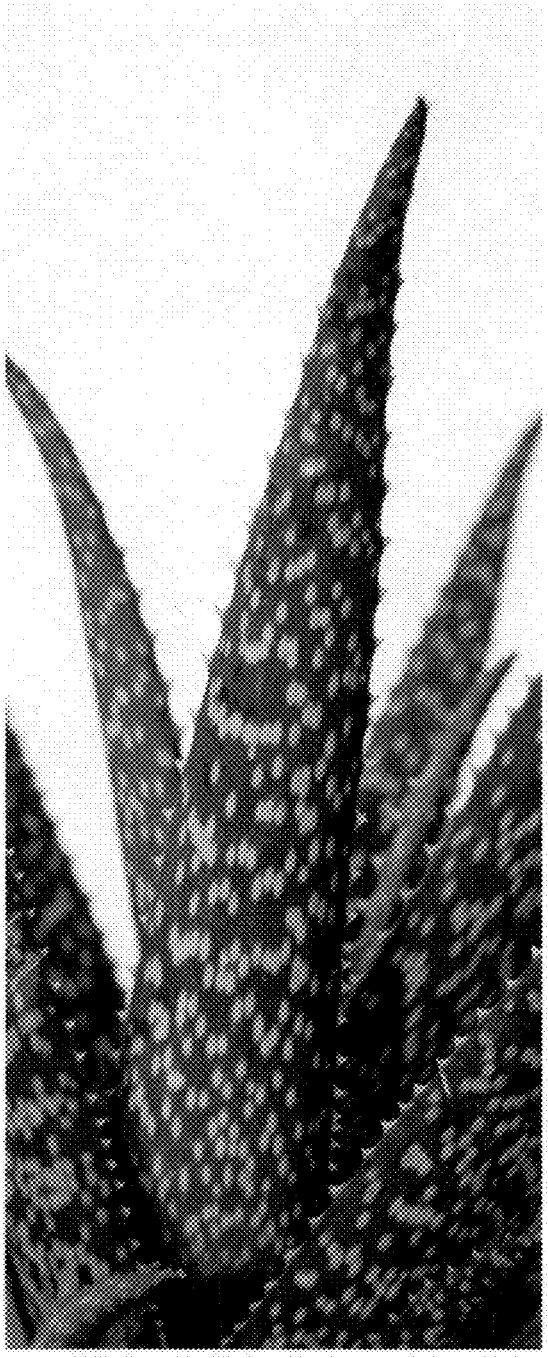
FIG. 3 illustrates, as nearly true as it is reasonably possible to make the same in color photographs of this type, the abaxial surface of the mature foliage of 'AMIAL2139'.

The following observations and measurements made in October of 2020 describe averages from a sample set of six specimens of 40-week-old 'AMIAL2139' plants grown in 14 cm nursery containers at commercial greenhouse in Honselersdijk, the Netherlands. Plants were produced using conventional greenhouse production protocols for *Aloe* which consisted of minimal overhead irrigation, minimal fertilizer applications, and control measures for common pests and diseases. No photoperiodic treatments or artificial light was given to the plants.

Those skilled in the art will appreciate that certain characteristics will vary with older or, conversely, with younger plants. 'AMIAL2139' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, Sixth Edition.

A botanical description of 'AMIAL2139' and a comparison with the parent plants and the closest known commercial comparator is provided below.

Plant description:

*Growth habit*.—Succulent perennial with foliage growing in a basal rosette; secondary rosettes are eventually produced at the base, themselves eventually forming a short stem. Succulent perennial with foliage growing in a basal rosette; secondary rosettes are eventually produced at the base of the plant; 14 secondary rosettes observed.

*Plant shape*.—Basal rosette.

*Height from soil level to top of foliar plane*.—24.6 cm.

*Plant spread*.—Average of 37.3 cm.

*Growth rate*.—Moderately to highly fast growing.

*Plant vigor*.—Highly vigorous.

*Propagation*.—Type — Leaf cuttings. Time to initiate rooting — Approximately 21 days at 18 degrees Celsius. Crop time — Approximately 60 weeks to produce a marketable plant in a 14 cm container.

*Disease and pest resistance or susceptibility*.—Similar to other *Aloe* varieties.

*Environmental tolerances*.—Adapt to, at least, USDA Zones 10 to 12 and temperatures as high as 40 degrees Celsius; low tolerance to rain; high tolerance to wind.

Root system:

*General*.—Fine, well-branched fibrous roots.

Stems: No stems observed at this date.

Foliage:

*Arrangement*.—Spiraled.

*Division*.—Simple.

*Attachment*.—Sessile.

*Quantity*.—Approximately 16 leaves per rosette.

*Shape*.—Lanceolate; succulent.

*Dimensions*.—26.1 cm long, 4.5 cm wide, and 1.1 cm thick, on average.

*Aspect*.—Flattened terete.

*Attitude*.—Flat to very slightly concave; leaf-bases are nearly horizontal, leaf blades curve upwards from the base at an average angle of 45-degrees with an apex that curves slightly downward at an average angle of 20-degrees to the leaf blade.

*Apex*.—Long and narrow acuminate.

*Base*.—Broad cuneate.

*Margin*.—Dentate; not undulated or lobed. Spines have an average length of 0.25 cm and are colored light greyed-green, nearest to RHS 192B and 192C, and lightly suffused with greyed-orange at the tip, closest to a mixture of RHS N170B and N170C.

*Texture, adaxial surface*.—Smooth, glabrous, and densely covered with oblong protuberances, each approximately 0.5 cm in length and 0.2 cm in width.

*Texture, abaxial surface*.—Smooth, glabrous, and densely covered with oblong protuberances, each approximately 0.45 cm in length and 0.2 cm in diameter; spots are irregularly arranged in highly irregular transverse rows.

*Luster, adaxial surface*.—Matte.

*Luster, abaxial surface*.—Matte.

*Color*.—Juvenile foliage, adaxial surface — Green, a blend of RHS 137C and 143A; protuberances are yellow-green, nearest to 145C. Juvenile foliage, abaxial surface — Green, a blend RHS 143A and 143B; protuberances are yellow-green, nearest to 145C. Mature foliage, adaxial surface — Green to yellow-green, slightly darker than a blend of RHS NN137A and 147A; protuberances are yellow-green, nearest to 147D. Mature foliage, abaxial surface — Green, nearest to RHS NN137A, with a greyed-green shine, nearest to 191A; protuberances are yellow-green, nearest 148D. Venation — No venation visible.

Inflorescence: No flowering has been observed to date.

COMPARISONS WITH THE PARENT PLANT

Plants of the new cultivar 'AMIAL2139' differ from the seed parent, an unnamed interspecific *Aloe* hybrid plant (not patented), in the following characteristics described in Table 1 below.

TABLE 1

| Characteristic | 'AMIAL2139' | The seed parent. |
|---|---|---|
| Foliage size. | Larger than the seed parent. | Smaller than 'AMIAL2139' |
| Foliage attitude. | More upright than the seed parent. | More relaxed than 'AMIAL2139'. |

Plants of the new cultivar 'AMIAL2139' differ from the pollen parent, an unnamed *Aloe vera* (not patented), in the following characteristics described in Table 2 below.

TABLE 2

| Characteristic | 'AMIAL2139' | The pollen parent. |
|---|---|---|
| General color- of the foliage. | A darker shade of green, relative to the pollen parent. | A lighter shade of green, relative to 'AMIAL2139'. |
| Size. | Smaller than the pollen parent. | Larger than 'AMIAL2139'. |
| Size of foliar protuberances. | Smaller than the pollen parent. | Larger than 'AMIAL2139'. |
| Abundance of foliar protuberances. | Less abundant. | More abundant. |

COMPARISONS WITH THE CLOSEST KNOWN COMPARATOR

Plants of the new cultivar 'AMIAL2139' differ from the interspecific hybrid, *Aloe* plant 'AMIAL2136' (U.S. Plant Pat. No. 36,929) in the following characteristics described in Table 3 below.

TABLE 3

| Characteristic | 'AMIAL2139' | 'AMIAL2136' |
|---|---|---|
| Foliage abundance. | More abundant than 'AMIAL2136'. | Less abundant than 'AMIAL2139'. |
| Foliage size. | Smaller than 'AMIAL2136'. | Larger than 'AMIAL2139'. |
| Presence of foliar Protuberances. | Both the adaxial and abaxial foliar surfaces of all foliage are densely covered with oblong pro-tuberances. pro-tuberances arranged in irregular longitudinal rows. | The adaxial surface is devoid of pro-tuberances and the abaxial surface of the oldest leaves are sparsely to moderately covered with small orbicular pro-tuberances. |

That which is claimed is:

1. A new and distinct variety of *Aloe* plant named 'AMIAL2139', substantially as described and illustrated herein.

* * * * *